United States Patent [19]

Ulich et al.

[11] Patent Number: 5,257,085
[45] Date of Patent: Oct. 26, 1993

[54] SPECTRALLY DISPERSIVE IMAGING LIDAR SYSTEM

[75] Inventors: Bobby L. Ulich; Duane Smith, both of Tucson, Ariz.; R. Norris Keeler, McLean, Va.

[73] Assignee: Kaman Aerospace Corporation, Bloomfield, Conn.

[21] Appl. No.: 690,767

[22] Filed: Apr. 24, 1991

[51] Int. Cl.$^5$ .................. G01N 21/64; G01N 21/65; G01J 3/44
[52] U.S. Cl. ........................... 356/73; 356/301; 356/318; 356/328; 358/95
[58] Field of Search .............. 356/301, 317, 318, 326, 356/328, 73; 358/95

[56] References Cited

U.S. PATENT DOCUMENTS

| | | | |
|---|---|---|---|
| 3,625,613 | 12/1971 | Abell et al. | 356/301 |
| 3,723,007 | 3/1973 | Leonard | 356/301 |
| 3,768,908 | 10/1973 | Zaromb | 356/301 X |
| 3,788,742 | 1/1974 | Garbuny | 356/5 |
| 3,829,694 | 8/1974 | Goto | 356/301 X |
| 4,496,839 | 1/1985 | Bernstein et al. | 250/341 |
| 4,555,179 | 11/1985 | Langerholc et al. | 356/342 |
| 4,632,550 | 12/1986 | Hara et al. | 356/317 X |
| 4,718,761 | 1/1988 | Tsuchiya | 356/318 |
| 4,950,075 | 8/1990 | Ichinose et al. | 356/432 X |
| 5,026,160 | 6/1991 | Dorain et al. | 356/328 |
| 5,091,778 | 2/1992 | Keeler | 358/95 |

OTHER PUBLICATIONS

Sato et al, "Laser radar for remote detection of oil spills", Applied Optics, vol. 17, No. 23 (1 Dec. 1978), pp. 3798-3803.
Kobayashi et al "Laser-Raman Radar for Air Pollution Probe", Proc. of the IEEE vol. 58 #10, Oct. 1970, pp. 1568-1571.

Primary Examiner—Vincent P. McGraw
Attorney, Agent, or Firm—Fishman, Dionne & Cantor

[57] ABSTRACT

An imaging UV/visible fluorosensing and Raman lidar system comprises an optical sensor for simultaneously measuring temporally, spatially and spectrally resolved laser backscatter from on the land, on or beneath the surface of bodies of water and in the atmosphere. The present invention utilizes "active" interrogation or "passive" interrogation for remotely and non destructively probing the spectrally-dependent optical properties of a scene. In the "active" mode, the optical sensor of this invention comprises a transmitter (preferably a tunable solid state laser) which emits pulses of coherent light through a variable or adjustable field-of-view telescope whereupon the light pulses are then propagated towards a scene (e.g., land, sea or atmosphere). Thereafter, laser backscatter is collected by a second variable field-of-view telescope and directed to an imaging system and spectrally dispersive optical subsystem.

59 Claims, 4 Drawing Sheets

SPECTRALLY DISPERSIVE IMAGING LIDAR SYSTEM

BACKGROUND OF THE INVENTION

This invention relates generally to an imaging lidar (light detection and ranging) system. More particularly, this invention relates to an imaging UV/visible fluorosensing and Raman lidar system having the ability to simultaneously measure temporally, spatially and spectrally resolved laser backscatter from on the land, on or beneath the surface of bodies of water and in the atmosphere.

There are numerous civilian and military applications which require or could benefit from the remote and non-destructive sensing and probing of the spectrally-dependent optical properties of a scene. Such applications include (1) detection and classification of oil spills and oil seepage on land and the ocean; (2) remotely measuring the atmospheric release of a pollutant or a target chemical such as a chemical associated with illegal drug production and chemical warfare agents (which might be monitored in a treaty verification control agreement or on a battlefield); (3) the measurement of sub-oceanic surface biogenic fluorescence spectra or differential reflectance spectral images in a complex scene to enhance object or substance detection; (4) measurement of wavelength dependent fluorescence decay laws and performance of spontaneous and stimulated Raman spectroscopy to measure such parameters as water temperature, sea salinity, water turbidity (due to gaseous or solid dispersements), subsurface chemical pollution as well as performance of vibrational spectral identification of hydrocarbons and target chemicals.

Prior art methods are known for the remote probing of the spectrally dependent optical properties of a scene. Such prior art uses either "passive interrogation" where the sensor system casts no light of its own upon the land, sea or atmosphere; or "active interrogation" wherein an intense narrow spectral bandwidth light source, such as a laser, probes the optical properties of the different media. Examples of such "active" systems are described in "Laser Remote Sensing" by Raymond M. Measures, published by John Wiley & Sons, Inc. (1984). In general, while these prior art "active" systems have the ability to perform measurements of temporally resolved spectral reflectance, fluorescence and Raman scattering, such prior art "active" systems are deficient in their inability to produce quantitative areal, volumetric, radiometric and spectrometric imagery of a scene with geodetic measurements. Examples of passive remote sensing systems are described in F. E. Hoge, R. N. Swift and J. K. Yungel, "Active-Passive Ocean Color Measurements: 2 Applications", Appl. Opt. 25 (1986) 48–57.

Sensor systems for remote detection and imaging of objects in a backscattering medium are known and described in, for example, U.S. Pat. Nos. 4,862,267, 4,964,721, 4,967,270, 5,013,917 and U.S. Ser. No. 565,631 filed Aug. 10, 1990, all of which are assigned to the assignee hereof and fully incorporated herein by reference. In general, these imaging lidar systems utilize one or more laser transmitters which generate short pulses of light and project these pulses down toward an object or target enveloped by a backscattering medium. One or more gated camera receivers detect the pulses of light reflected from the target after an appropriate time delay. These detected reflected pulses of light are then converted to a video image of the target.

While well suited for their intended purposes, the above-mentioned imaging lidar systems generally do not have the ability to perform measurements of temporally resolved spectral reflectance, fluorescence and Raman scattering. As discussed, there is a perceived need for such measurements; and therefore known imaging lidar systems are not adequate in this regard.

SUMMARY OF THE INVENTION

The above-discussed and other drawbacks and deficiencies of the prior art are overcome or alleviated by the imaging UV/visible fluorosensing and Raman lidar system of the present invention. In accordance with the present invention, an optical sensor is provided for simultaneously measuring temporally, spatially and spectrally resolved laser backscatter from on the land, on or beneath the surface of bodies of water and in the atmosphere. The present invention utilizes "active" interrogation or "passive" interrogation for remotely and non-destructively probing the spectrally-dependent optical properties of a scene.

In the "active" mode, the optical sensor of this invention comprises a transmitter (preferably a tunable solid state laser) which emits pulses of coherent light through a variable or adjustable field-of-view telescope whereupon the light pulses are then propagated towards a scene (e.g., land, sea or atmosphere). Thereafter, laser backscatter is collected by a second variable field-of-view telescope and directed to an imaging system and spectrally dispersive optical subsystem. The light collected for the imaging system is focussed through either a laser bandpass or laser line filter onto the face of a time-gated image intensifier followed by a charge-coupled device (CCD) camera. The light collected for spectral dispersion subsystem is anamorphically demagnified to a slit-shape and subsequently fed into an input slit on a spectrometer (e.g., a flat-field monolithic spectrograph or cascaded prism dispersers followed by a streak camera). The output of the spectrometer is focussed onto the photocathode of an intensifier and CCD camera as in the imaging system. The digitized output of the spectrally dispersive and imaging systems is sent to a computer, where data is concurrently logged on the laser wavelength, geodetic position, time-gate and range information, laser power, intensifer gains and other information relevant to remote sensor operation. The data may then be stored in analog or digital video format.

The optical sensor described above includes at least three different operating modes, namely imaging, fluorosensing and Raman detection. The present invention provides an improved technique for performing imaging, fluorosensing and Raman detection relative to prior art techniques in that in addition to its ability to perform measurements of temporally resolved spectral reflectance, fluorescence and Raman scattering, it can provide quantitative imagery of a scene with geodetic measurements.

In accordance with a feature of this invention, the spectrometer is preferably either a cascaded prism disperser(s) followed by a streak camera, prismatic predispersers or a monolithic spectrometer. In the latter case, the monolithic spectrometer is comprised of a single piece of glass, plastic and other optical materials that are permanently bonded together and fabricated from focussing lenses, diffraction gratings, prismatic pre-dispersers, laser line filters and entrance/exit slits. The one-piece integral design of this spectrometer is an important feature of the present invention in that this invention is well suited for applications in dusty, high vibration environments over large temperature ranges.

The above-described and other features and advantages of the present invention will be appreciated and understood by those of ordinary skill in the art from the following detailed description and drawings.

BRIEF DESCRIPTION OF THE DRAWINGS

Referring now to the drawings, wherein like elements are numbered alike in the several FIGURES.

DESCRIPTION OF THE PREFERRED EMBODIMENT

Figure 1:
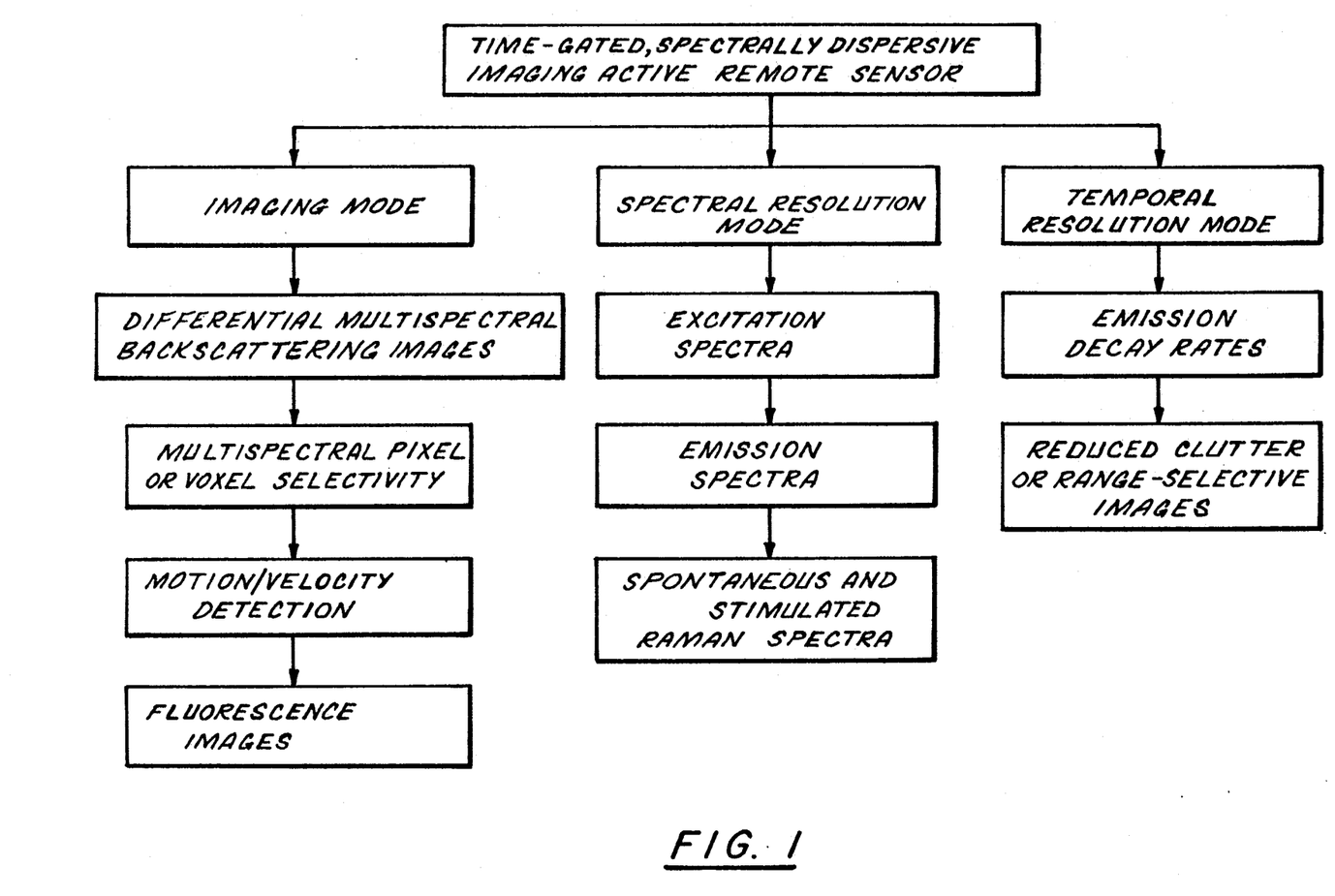
FIG. 1 is a flow chart depicting the several operational modes and sub-modes for the optical sensor of the present invention.

The present invention comprises an optical sensor which remotely and non-destructively probes the spectrally, temporally and distance-dependent optical properties of a scene. FIG. 1 is a flow chart depicting the functions or operational modes of this invention (referred to as a Time Gated, Spectrally Dispersive Imaging Active Remote Sensor).

There are essentially three different major modes of operation for the present invention: imaging, fluorosensing and Raman detection. There are also ancillary operational modes for each of the major modes (as described in FIG. 1). While it is recognized that these operational modes may, under some circumstances, have significant overlap in the operation of the present invention, these modes are useful for broad descriptive categorization of the end use of this invention. Prior to describing each of these operational modes in detail, the components (or hardware) of the remote sensing system of this invention will be described with reference to FIG. 2.

Figure 2:
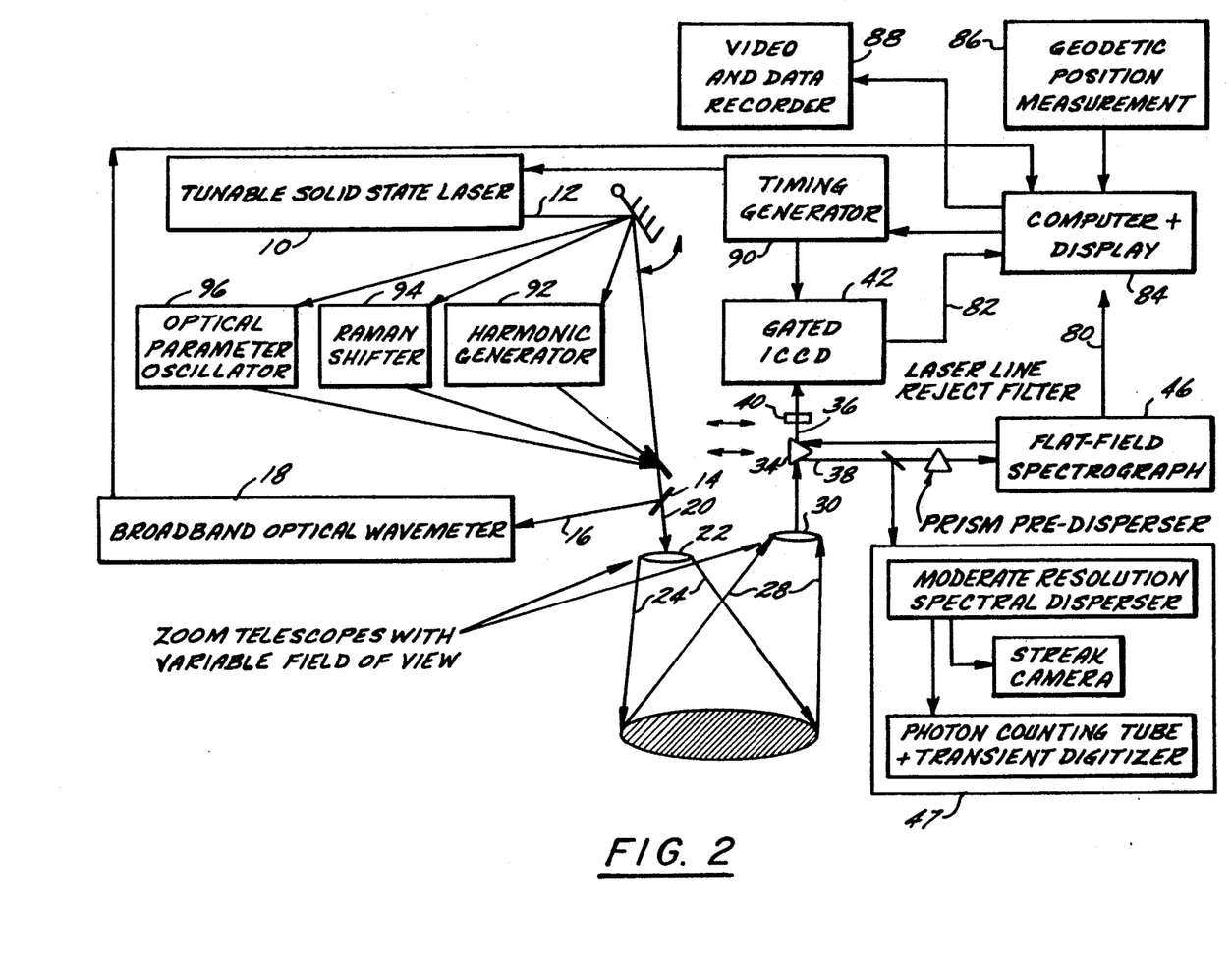
FIG. 2 is a block schematic diagram depicting the structural components for the optical sensor of the present invention.

The present invention is schematically shown in the block diagram of FIG. 2. The optical train begins with the output 12 of a tunable solid state laser 10. A tunable solid state laser 10 whose gain medium has a small thermal lens constant is preferred in order to have the added capability of variable repetition rate and probe wavelengths. More conventional laser technology lasers such as $Nd^{3+}$:YAG pumped by flashlamps (where constant laser repetition rate is critical to maintain stable operation) are less desirable for this invention than diode or flash lamped pumped tunable solid state lasers. At present, variable repetition rate, tunable, $Ti^{3+}$:$Al_2O_3$ (titanium sapphire), $Cr^{3+}$+BeAlO$_x$ ("Alexandrite") or $Cr^{3+}$:LiSrAlF$_6$ lasers appear to be the most appropriate contemporary laser technologies. It may be most desirable to utilize a tunable optical parametric oscillator. Detailed examples of suitable tunable solid state lasers are described in U.S. application Ser. No. 632,377, filed Dec. 21, 1990, assigned to the assignee hereof and incorporated herein by reference.

The laser light 12 is directed into a beam splitter 14, where a small portion 16 of the light is sent to a broad band laser wavemeter and power monitor 18 (such as a thermopile or rapid response pyroelectric joule meter) to continuously monitor laser 10. The high temporal bandwidth joule meter 18 is important in that it accurately measures the outgoing laser pulse energy thereby facilitating absolute radiometric assessment of the backscatter magnitude. The remainder of the laser light 20 is sent to a first adjustable field-of-view telescope 22 and propagated at 24 towards a scene 26, which could be land, sea or atmosphere. Then, laser backscatter 28 is collected by a second telescope 30 with a variable field-of-view, which under most circumstances matches that of the telescope 22. In an alternative embodiment, a single variable field-of-view telescope may be used in place of the discrete telescopes 22, 30. A suitable field-of-view telescope may have a field-of-view of 10 milliradians and a 24 inch collecting aperture. The collecting telescope output 32 is then directed by a mirror or beam splitter 34 to an imaging system (at 36) and a spectrally dispersive optical subsystem (at 38).

Collected light 36 that goes to the imaging system is focussed through a laser bandpass filter 40 onto the face of a gated camera 42 comprised of a timed-gated image intensifier followed by a charge-coupled device camera. Camera 42 is described in more detail in FIG. 4 of aforementioned U.S. Pat. No. 4,862,257.

Figure 3:
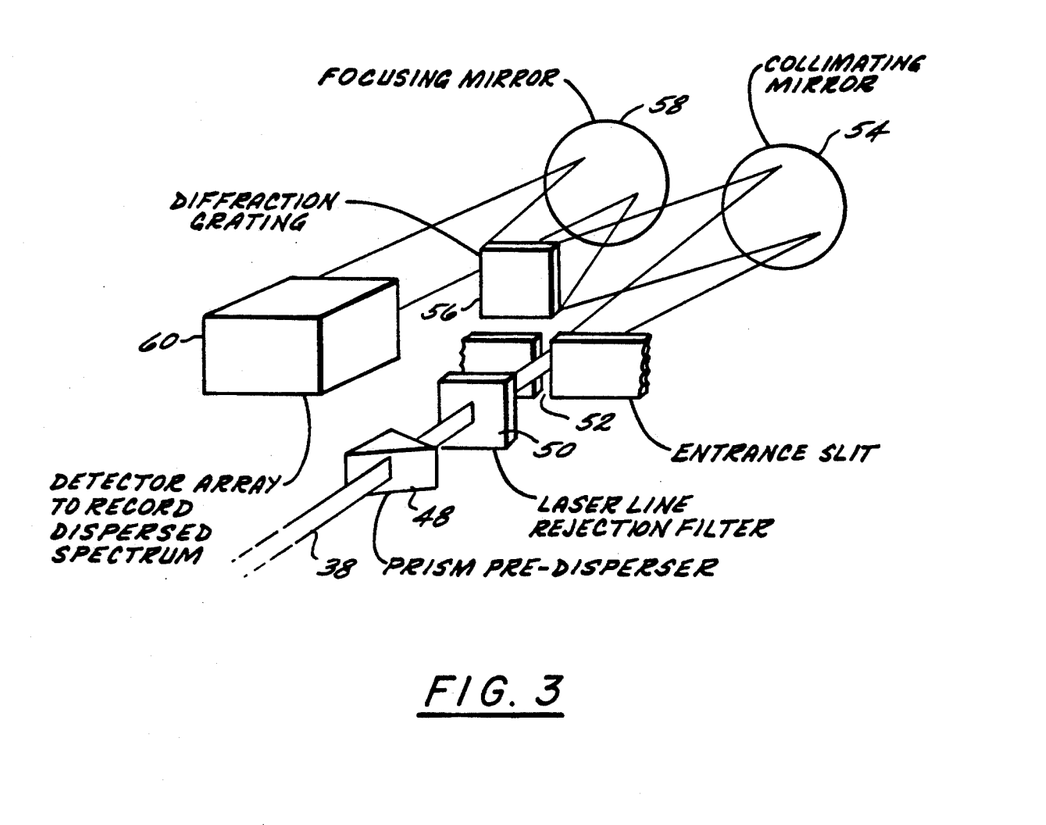
FIG. 3 is a schematic diagram of a spectrograph with a line filter as its input.
Figure 4:
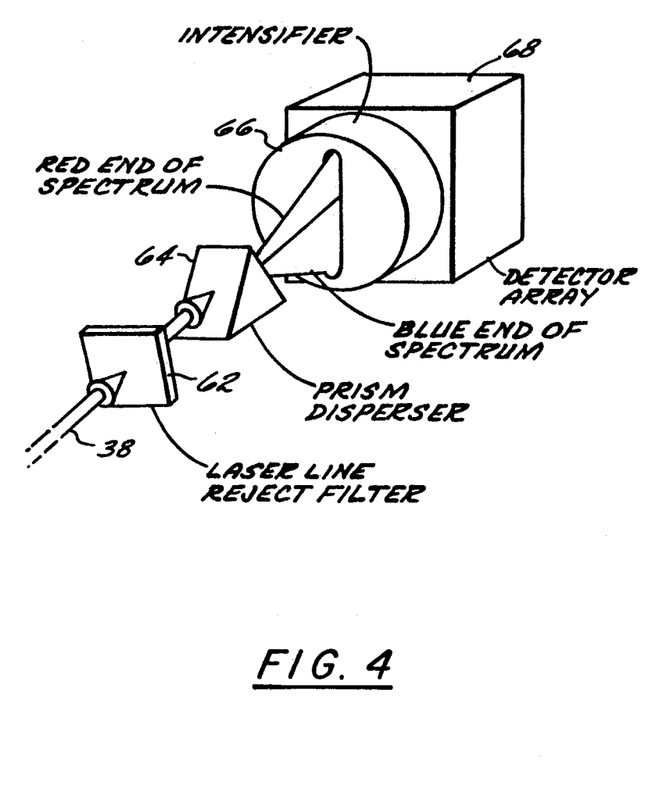
FIG. 4 is a schematic diagram of a prism spectrograph with an intensified detector array.

Light 38 that is collected for spectral dispersion is anamorphically demagnified to a slit-shape using either prisms, astigmatic lenses or preferably a fiber optic bundle; and subsequently fed into an input slit on a spectrometer 46. The output of the spectrometer 46 is then focussed or fiber optically coupled onto the photocathode of an intensifier and CCD camera 42. Alternatively, light 38 is sent to a temporally and spectrally resolved optical subsystem identified generally at 47. FIGS. 3 and 4 depict various embodiments of suitable hardware assemblies for such spectral dispersion. FIG. 3 depicts a spectrograph with a line filter as its input while FIG. 4 depicts a prism spectrograph with an intensified detector array. In FIG. 3, light 38 is delivered to a prism pre-disperser 48 followed by a laser line rejection filter 50 and an entrance slit 52. The light is then reflected off a collimating mirror 54 to a diffraction grating 56. In turn, the light is sent to a focussing mirror 58 and finally to a detector array 60 to record the dispersed spectrum.

In FIG. 4, the light 38 is delivered to a laser line rejection filter 62 followed by a prism disperser 64. The output from prism disperser 64 is then delivered to an intensifier 66/detector array assembly 68.

Spectrometer 46 may also comprise a single piece of glass, plastic and other optical materials that are permanently bonded together and fabricated from focussing lenses, diffraction gratings, prismatic pre-dispersers, laser line filters and entrance/exit slits as described in U.S. patent application No. 417,623 filed Oct. 4, 1989 entitled "Monolithic Optical Programmable Spectrograph", (now U.S. Pat. No. 5,026,160) the entire contents of which is incorporated herein by reference. The one piece integral design of the spectrometer disclosed in U.S. patent application Ser. No. 417,623 (now U.S. Pat. No. 5,026,160 is well suited for use in this invention in that the present invention is particularly useful in dusty, high vibration environments over large temperature ranges. Prior art standard design spectrometers, such as double and triple Raman spectrographs would be difficult to qualify for airborne applications or to military specifications.

Figure 5:
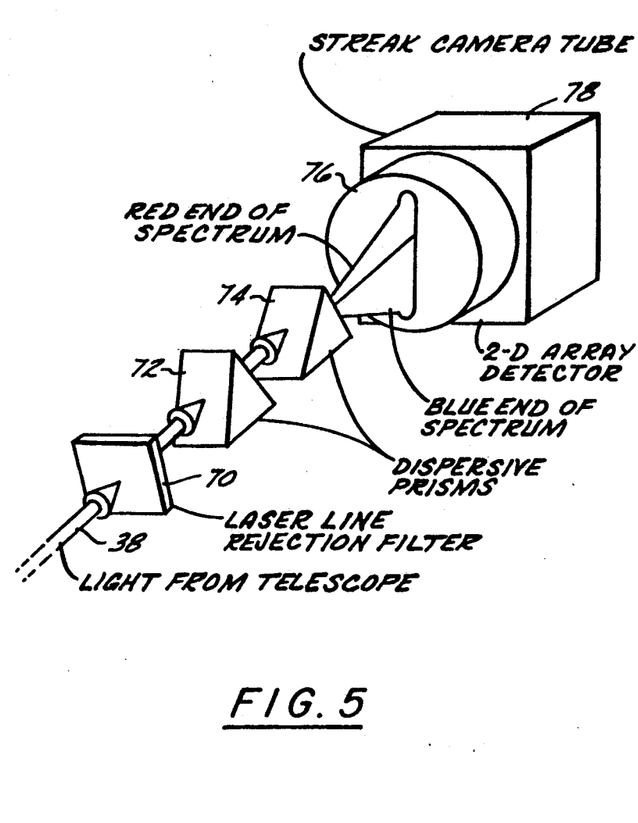
FIG. 5 is a schematic diagram of a temporally and spectrally resolved emission detection system with cascaded prism disperser and streak camera.

As mentioned, light 38 may also be directed to a temporally and spectrally resolved optical subsystem 47. Subsystem 47 utilizes a spectrograph shown in detail in FIG. 5. In FIG. 5, light 38 is fed to a laser line rejection filter 70 and then through a pair of cascaded dispersive prisms 72, 74 to a streak camera tube 76 and a two dimensional detector array 78.

Referring again to FIG. 2, the digitized outputs 80, 82 from the spectrally dispersive system and from the imaging system are sent to a computer 84, where data is concurrently logged on the laser wavelength, geodetic position (see item 86), time-gate delay and range, laser power, intensifier gains and other information relevant to remote sensor operation. The data may be stored in analog or digital video format in recorder 88 on industry standard magnetic cassette tapes.

With reference to both FIGS. 1 and 2, in the first major mode of operation of this invention known as "imaging", backscattered light is collected by the telescope 30 and then focussed onto intensified charge-coupled device camera 42. The intensifier is time gated by timing generator 90 to differentiate and select the laser backscatter or time delayed fluorescense from the scene. Time-gating can be useful to reduce the apparent clutter in a "deep" scene composed primarily of opaque objects. Time gating can also be used to set the probed voxel size (volume element as opposed to an area element in the case of a pixel) in partially transmissive materials such as in the ocean and in the atmosphere. The probed voxel size in the ocean (possibly subsurface) or the atmosphere is selected by controlling the gate width and delay on the intensifer. These features of imaging lidar systems are well known. However, in accordance with an important and novel feature of this invention, the wavelength-dependent differences in the image intensity patterns that the camera measures for the target scene are utilized to achieve a heretofore novel imaging measurement. For certain scenes, scanning the laser wavelength may be useful to improve the intrascene contrast. For example, in covert search and rescue operations, the party being sought or rescued could have a large flag that appears as camouflage in the visible, but has a strong near-IR or UV reflectivity that would be entirely unnatural and be easy to detect during the day or the night. Another example is to measure the particulates above an industrial smoke stack versus above a nearby field to detect small particles which have strong UV backscatter and weak visible backscatter. To take advantage of such multi-spectral image detection scenarios, the present invention utilizes broad wavelength control either by scanning the fundamental wavelength of the solid state laser and/or scanning the frequency doubled and frequency tripled outputs of the laser (see item 92 in FIG. 2). Wavelength control may also be accomplished by the use of Raman shifters 94 or parametric oscillators 96.

The laser wavelength may be scanned by a variety of mechanisms. Some examples include intracavity electro-optic tuning, or multiple resonator arms selected by electro- or acousto-optic selectors. Other tuning technologies such as Lyot filters, diffraction gratings or cascaded prisms may also be utilized although they are more difficult to package to be robust for use on high vibration platforms such as helicopters or all-terrain vehicles. Mechanically tuned dispersive or diffractive tuning elements would also be less likely to be amenable to high tuning speeds, such as tuning within a laser pulse or between laser pulses that would come out in a pulse train or high repetition rate burst.

In a second major mode of operation, the light collected by the receiving telescope is spectrally dispersed. The light 38 delivered into spectrometer 46 is analyzed in several ways to detect excitation spectra, emission spectra and spontaneous and stimulated Raman spectra. One analytic probe technique is to fix the wavelength of the laser that excites the fluorescence and to measure the spectrum of the emission that is collected. This is fluorescence/phosphorescence emission spectroscopy which can be used to detect the chemical species present by comparing the spectra of different molecules.

However, sometimes the electronic emission spectra can be broad and nearly featureless, making it difficult to distinguish one class of molecules from another. This brings forth a second spectral analysis technique generically referred to as excitation spectra. A case in point for use of excitation spectra would be hydrocarbon oil slicks on the ocean's surface. To improve the ability for identification of different parameters of oils from their broad emission spectra, the present invention changes the wavelength of the laser that is exciting the fluorescence and again records the emission spectrum (producing the so-called "excitation spectra"). Measuring how the emission spectrum changes with exciting wavelength can be useful in distinguishing what would otherwise appear to be similar molecular emission spectra. Further information about the molecule's identity and its electronic energy level structure is obtained because the excitation spectra depend upon the energy and bandwidth of dark (low emission quantum yield) higher energy states that absorb the laser light. Moreover, the excitation spectra are influenced by the wavelength dependence of energy transfer among the molecular states, further assisting in identification of the molecule. When measuring the fluorescence emission or excitation spectra, this invention will gate the camera's intensifier "on" after the diffuse and specular backscatter from the laser arrives at the collecting telescope's aperture. Time-gating in this manner will help in rejecting the backscattered laser light which is unshifted in wavelength. Alternatively, at the beginning of an emission or excitation spectra scan, it is straightforward to time gate the intensifier to intentionally collect the laser backscatter to reject the fluorescence and perform a relative wavelength calibration of the data set. Thus, the present invention will record the wavelength of the laser, as the spectrometer sees it. A more accurate calibration of the laser will be derived from the broadband laser wavemeter 8, which is constantly measuring the laser wavelength and reporting it to the control computer 84. By comparing the output of the wavemeter and the spectrometer, the possibility of optical misalignment causing misidentification of the molecular emission spectrum will be reduced (this is important, especially when trying to distinguish oil slick spectra that are similar in shape and only small spectral shifts are measurable within the signal-to-noise constraints).

A third variation of the second major mode of operation of this invention which employs spectral resolution is stimulated or spontaneous Raman spectra. The present invention introduces optical techniques to facilitate the traditionally difficult-to-obtain Raman scattering spectra for a remote sensing application. The two principal challenges in obtaining adequate signal-to-noise ratio Raman spectra are to eliminate the spectral wings of the scattered laser light and to obtain enough backscattered photons. First, to help eliminate the scattered laser light, a highly effective, spectrally narrow laser line rejection filter is inserted into the optical path, either before the spectrometer (see FIGS. 3 and 4) or the intensifier (see FIG. 2), depending upon the needs for a given configuration. Preferred line rejection filters (such as are available from Physical Optics Corporation, Torrance, Ca.) are based on volume holograms and provide optical densities of 5 to 6 at the chosen laser wavelength with a greater than 60% transmission as close as 45 cm$^{-1}$ to the laser line. The filter's transmission band has a fairly uniform transmission for several thousand wavenumbers to the red of the laser which is well-suited for measurement of the vibrational Raman spectrum. With a highly efficient laser line filter, a single holographic grating spectrometer can achieve laser line rejection of greater than $10^{10}$. If necessary, a prism pre-disperser can be used in front of the spectrometer entrance slits to further enhance the laser line rejection. The present invention utilizes this novel configuration for the spectrometer to avoid the use of double and triple spectrometers traditionally used in Raman spectroscopy. It is well known that compound, multiple spectrometers are large, heavy and susceptible to optical misalignment in high vibration and hostile environments.

As is clear from the foregoing description, the spectrally dispersive portion of the optical system of this invention may be configured in several different ways. The configuration chosen for a given embodiment of the invention will depend in part upon the final intended use of the sensor. For example, if the predominant use of the sensor is to record the Raman scattering spectrum in the active probe mode (the laser is on), it will be necessary to use a moderately high dispersion spectrometer with an enchanced ability to reject the laser wavelength. As scattered laser light is always a concern in Raman spectroscopy, it will be necessary to reject the laser line backscatter to the maximum extent possible (typically a rejection of no less than $10^{-7}$ to as much as $10^{-14}$) while still being able to look for Raman backscattering from, for example, 50 to 2000 wavenumbers to the red side of the laser wavelength. These resolution and rejection requirements can be met with a single grating spectrometer which has a prism pre-disperser, a holographic line-reject filter or both as shown in FIG. 3. The grating spectrometer as shown in FIG. 3 has an entrance slit, collimating mirror, diffraction grating and focussing mirror that spectrally disperses the collected light across a photon counting detector array. Alternatively, the grating spectrometer ultimately may differ from that shown in FIG. 3 in that it may be two or three grating spectrometers combined into additive or subtractive dispersion configurations in order to enhance the resolution and stray light rejection. However, it is believed that no more than one spectrometer should be used due to the increased mass, volume and alignment problems that accrue with more complicated spectrometers. The spectrometer (or spectrometers) used may be based upon the monolithic configuration of U.S. application Ser. No. 417,623 in order to enhance the physical robustness of the sensor system.

However, if the remote sensor system is only required to measure very broad emission spectra without sharp spectral structure (for example, 350 to 700 nm wavelength with peaks no narrower than many 10's of nm), then the most appropriate spectral disperser may be a laser line reject filter (to prevent saturation of the detector response in wavelength regions near the laser wavelength) followed by a prism spectrograph and an array detector (see FIG. 4). The prism spectrograph may be a single prism which disperses the input beam or it may be a series of cascaded prisms, (each prism further dispersing the output of the previous prism) in order to increase the spectral resolution.

The present invention will produce additional enhancement of the spontaneous Raman scattering spectrum signal-to-noise ratio by using the time gated intensifier to reject the longer lived backscattered fluorescence (spontaneous Raman scattering will follow the pulse shape of the laser). Because the spontaneous vibrational Raman scattering cross-sections are typically 3 to 6 orders of magnitude less than spontaneous electronic emission spectra, this invention will use the adjustable field-of-view transmitting and receiving telescopes 22, 30 to increase the laser power density and reject background optical noise. This invention will also use non-linear optical techniques (such as frequency doubling and tripling) of the laser to produce different (i.e., shorter) wavelengths in order to take advantage of (a) the (wavelength)$^{-4}$ non-resonant scaling of the spontaneous scattering cross-section; and (b) potential resonance enhancement of the Raman scattering cross-section, which can increase the apparent Raman scattering cross-section by several orders of magnitude. It will be appreciated that without the ability of this invention to temporally gate the spectrally dispersed light that is collected, the Raman spectra intensity can be easily overwhelmed by the fluorescence intensity, thereby reducing the utility of resonant cross-section enhancement. Therefore, time gate rejection of the fluorescence combined with the use of excitation source blue shifts and resonance cross-section enhancement, holographic gratings, holographic laser line filters, prism pre-dispersers and variable field-of-view telescopes give the present invention significant new advantages in obtaining spontaneous Raman scattering spectra in remote sensing.

The present invention will also be capable of measuring stimulated Raman spectra by reducing the size of the laser beam and narrowing the field-of-view of the collecting telescope to match the transmitted laser beam. Although the threshold for backward stimulated Raman can be high in some media, such as opaque solid matter, short-range stimulated Raman backscattering is anticipated to be useful in transparent scenes, such as the atmosphere and in the ocean. With a multi-joule short wavelength laser and the fact that stimulated Raman backscattering is not isotropic, the present invention is, with its spectrometer system, able to obtain the coherent Raman scattering spectrum.

It will be appreciated that a disadvantage of a gated intensifier for use in spectroscopy is that it may have a small dynamic range if the gain on the intensifier is high. A worst case dynamic range of, for example, 16:1, would make it difficult to quantitatively distinguish molecules that have broad, structureless spectral emission. However, in the case of vibrational Raman spectroscopy, the spectra are generally composed of many narrow lines whose position is the key issue for identifying a molecular species. Thus, for Raman spectroscopy, the limited dynamic range of the gated intensifier tube at high gain is less of an impediment.

In a third major mode of operation of the present invention, a narrow time gate is used on the intensifier. Sweeping the delay of the intensifier with respect to laser Pulses allows measurement of the fluorescence decay. This temporal decay could either be spatially resolved (an image), or spectrally resolved, or a combination of the two. For example, a temporally resolved image of broadband plankton fluorescence (using a laser line rejection filter on the camera) beneath the surface of the ocean may be helpful to localize or demonstrate the existence of flourishing areas or ecological damage. These fluorescence decay images may also be used to distinguish the different types of plankton present or to help measure triboluminescence. In another mode of operation, the collected light could be fed into the spectrometer instead of the imaging system. The spectrometer disperses different wavelengths across the input of the intensifier tube, and taking several snapshots of the spectrum as a function of delay from the laser pulse allows one to measure the temporal decays at different wavelengths in parallel. Wavelength-dependent decay constants have been demonstrated to be useful in oil slick characterization.

If it is necessary to measure the temporal decay of the laser-induced emission from the scene, then the sensor of this invention can be extended to measure the wavelength resolved emission spectra as well as measuring the temporal decay of the emission at each wavelength resolution element. This dual measurement of the wavelength resolved and temporally resolved emission can be achieved by optically coupling the light from the collecting telescope (in a non-imaging mode) to a spectrograph and streak camera as shown in FIG. 5. All of the light collected from the scene by the telescope is demagnified into a small spot. That small spot of light is then put through one or more (thus "cascaded") dispersive prisms to ultimately produce a slit-shaped illumination on the streak camera photocathode. Because of the dispersion of the prism, one end of the slit of light will have the blue-edge of the spectral band chosen and the other end of the slit of light will have the red edge of the spectral band with all intervening colors between the two ends. The streak camera will produce a two-dimensional record of the time-dependent emission at each wavelength on a 2-D array detector such as a CCD camera. One direction in the so-called streak record is wavelength and the other direction is chosen to be time after the laser pulse.

It may also be useful to couple the output of the somewhat higher spectral resolution grating spectrometer to the input of the streak camera (as opposed to the prism spectrometers). The increased spectral resolution, combined with the increased time resolution of the streak camera (10's to 100's of picoseconds) may be useful in cases where the remote sensor is acquiring a Raman scattering spectrum. The higher time resolution may be useful to narrow the detection system time gate and to reject ambient light (sunlight, moonlight, man-made light). If one assumes that the laser pulse width is less than the fluorescense decay time and that the laser penetration depth in the ocean is less than a few feet, this takes advantage of the fact that the temporal shape of the Raman backscattering from the oil follow the laser pulse shape (discounting coherent Raman effects) and the fluorescence decay is necessarily slower and does not follow the laser pulse shape.

There are many civilian and military applications for the present invention. In general, any scenario in which spectral and/or temporally resolved images of a scene need to be actively and remotely probed (active meaning that an illuminating laser is involved) can be addressed by this invention. Applications include detection and classification of oil spills and oil well seepage on land and the ocean. Another application is to remotely measure the atmospheric release of a pollutant or a target chemical such as a chemical associated with illegal drug production and chemical warfare agents (which might be monitored in a treaty verification control agreement or on a battlefield) over large areas/volumes in a reasonably short time frame (relative to prior art system). Other applications include the measurement of sub-oceanic surface biogenic fluorescence spectra (taking advantage of the ability to gate the imaging lidar return beneath the ocean's surface) or differential reflectance spectral images in a complex scene to enhance object or substance detection. Also, by the present invention's ability to spectrally and temporally resolve laser backscatter, one can measure wavelength dependent fluorescence decay laws and perform spontaneous and stimulated Raman spectroscopy to measure such parameters as water and air temperature, sea salinity, as well as perform vibrational spectral identification of hydrocarbons and target chemicals.

Still another application of this invention is object motion detection and velocity measurement by frame image differencing, or other image processing algorithms. For example, because some solid state lasers such as titanium sapphire can be operated at a variable repetition rate (micropulses or bursts of micropulses), it is possible to take a burst of sequential images of a scene believe to contain an object in motion (more than one camera may be required). The image processing computer would then, through differential edge enhancement or other image processing algorithm, calculate scene differences, taking into account platform motion. In a scene that is highly cluttered, lacks intrascene contrast or otherwise is difficult to see an image of a target in, frame-to-frame differencing may facilitate detection and classification of the object.

Still another use of this invention is to study fluid flow field dynamics with fluorescing tracers (the tracers may be small molecules, large dye molecules or specially prepared particulates). For example, one might release a tracer into the atmosphere or a body of water to study how prevailing conditions affect time-dependent dispersal of the tracer. Such studies may be used to help understand how heat and/or pollutants are dispersed from a smoke stack or a liquid discharge into the ocean. The method is brought to practice by exciting the tracer with one laser wavelength and by detecting the range gated images of a tracer emission at a different wavelength. Measuring the emission images at different times with different widths of range gates makes it possible to measure the spatial concentration profiles of the tracer as a function of time. It is important to point out that detection of the tracer emission at different wavelengths makes it possible to record tracer cloud shape without the sensor being overwhelmed by influence of laser backscatter from indigenous aerosols or hydrosols. In the event that the extant particle's and molecule's absorption spectra overlaps that of the tracer, it may be possible to use a different tracer or to shift the excitation and detection wavelengths in order to improve the signal-to-noise ratio of the images.

There are previously published examples of tracers being released in ocean fluorosensing studies (F. Hoge and R. N. Swift, "Absolute Tracer Dye Concentration Using Airborne Laser-Induced Water Raman Backscatter", Appl. Opt. 20 (1981) 1191-1202), but they did not use imaging lidar systems to perform the studies. Instead, this prior art used a conical scan mechanism that had a much lower area search rate and is not capable of forming high quality composite images due to noise sources such as changes in the sea surface, aircraft platform attitude fluctuations (Pitch, roll and yaw) and laser noise.

It will be appreciated that many variations to the preferred embodiments described herein may be employed in the present invention. For example, if the signal-to-noise ratio is not a serious limitation for a certain application, the mirror on the output of the collecting telescope may be replaced with a beam splitter that would direct the portions of the output simultaneously to the imaging and spectrally dispersive system. Or, depending upon the chemicals that are to be detected, it may be unnecessary or too costly to use a tunable laser as the light source and a smaller, less expensive fixed wavelength laser source may be chosen instead. Also, more than one transmitting laser (for example, each set at a different frequency) may be employed in this invention. Different tunable solid state lasers could be employed depending upon the types of molecules or organisms being probed. Similarly, the temporally gated camera technology chosen would depend upon the fluorescence emission and fluorescence decay properties of the chemicals that are being probed.

Another aspect of the optical design that would be subject to considerable variation would be the transmitting and receiving telescopes. One might choose to use the same telescope for the transmitter and receiver to minimize cost and maintain boresight accuracy during changes in the field of-view; alternatively if laser light scattering needs to be minimized, as would be the case in Raman LIDAR, the construction of this invention may be improved by the use of different optical trains for the transmitter and receiver.

As mentioned earlier, previous fluorosensors lacked the ability to combine measurements of the molecular emission spectra and its temporal decay with imaged-based area/volume measurements and geodesy. The present invention, as a measurement device, brings a unique capability for remote sensing of the concentration of a target molecule, substance or organism over large areas or volumes. The fluorosensor of this invention may be mounted in a truck, boat, aircraft or satellite.

The remote sensing system of this invention can function in either an active or a passive mode. In the active mode, the laser is used to stimulate an optical response from the medium (land, sea or air) such as luminescence or Raman scattering. In many situations, the stimulus-response probing by the sensor affords the greatest ability to discriminate between substances that luminesce. However, if eye safety, convert operations or other considerations make remote sensing by a probe laser undesirable, then passive remote sensing may be useful.

In the passive mode of operation, the laser does not emit light. The laser will not stimulate the medium with either continuous wave or pulsed light. In the passive mode, the sensor produces an image of the scene in its field of view through a pre-selected spectral bandpass filter, or it spectrally disperses the optical energy emanating from the scene without preserving the spatial information in a scene image. In the passive mode the scene must be actively emitting or reflecting ambient light without sensor intervention, as might occur in luminescence from oceanic microorganisms, fires in a forest or anthropogenic activity. In addition to recording a composite image of a scene within a selected spectral bandpass, it can also be useful to collect all of the light emitted by a scene, dispense with the image and spectrally disperse the light so as to obtain information about the nature of the optical emission/reflection activity. Such information may be useful in distinguishing different land based plant types from one another via their differential sunlight (or moonlight) reflection spectrum or to observe sub surface ocean triboluminescence or to monitor disturbances in the oceanic thermocline.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A method for remotely and non-destructively probing the spectrally, temporally and distance-dependent optical properties of a target volume using a single integrated optical sensor having multiple modes of operation including an imaging mode and a spectral analysis mode, including the steps of:
   - selecting a mode of operation for the optical sensor to operate in an imaging mode or a spectral analysis mode with said imaging mode including steps (a)-(e) and said spectral analysis mode including steps (f)-(i);
   - (a) selectively generating short pulses of light using laser transmitter means;
   - (b) projecting said short pulses of light toward the backscattering medium and at a target volume enveloped by the medium;
   - (c) receiving said pulses of light backscattered from said target volume after a time delay corresponding to the round-trip propagation time of said light pulses to and from said target volume using receiver means;
   - (d) converting said received pulses of light to a video image of said target defining a target volume image, said target volume image having an image intensity pattern associated therewith; and
   - (e) scanning the wavelength of the laser transmitter means to identify the wavelength-dependent differences in said image intensity pattern to thereby improve said video image of said target volume image;
   - (f) generating short pulses of light from laser transmitter means;
   - (g) projecting said generated short pulses of light toward a target volume;
   - (h) detecting said pulses of light backscattered from said target volume after a selected time delay using gated detector means; and
   - (i) spectrally analyzing said detected pulses of light in spectrometer means to create a selected spectra of said target volume.

2. The method of claim 1 wherein in said imaging mode:
   said laser transmitter means has an operating wavelength and includes means for tuning said operating wavelength.

3. The method of claim 1 wherein in said imaging mode said projecting step includes the step of projecting said pulses of light through a first variable field-of-view telescope and wherein said receiving step includes the step of:
receiving said reflected pulses of light in a second variable field-of-view telescope.

4. The method of claim 3 including the step of
maintaining the field-of-view in each of said first and second telescopes as equal.

5. The method of claim 1 wherein in said imaging mode said projecting step includes the step of projecting said pulses of light through variable field-of-view telescope means and wherein said receiving step includes the step of receiving said reflected pulses of light from said variable field-of-view telescope means.

6. The method of claim 1 wherein in said imaging mode said scanning step is controlled by at least one of the wavelength controlling means selected from the group consisting of harmonic generator means, Raman shifter means and optical parameter oscillator means.

7. The method of claim 1 wherein:
said selected spectra comprises emission spectra.

8. The method of claim 7 including the steps of:
selecting the operating wavelength of said laser transmitter means for excitation of fluorescence in said target volume; and
measuring the emission spectra to analyze said target volume.

9. The method of claim 8 wherein:
said emission spectra is analyzed for detection of chemical species in said target volume.

10. The method of claim 1 wherein:
said selected spectra comprises excitation spectra.

11. The method of claim 1 including the steps of:
selecting a first operating wavelength of said laser transmitter for excitation of fluorescence in said target volume;
measuring a first emission spectra of the excited target volume derived from said first operating wavelength;
selecting a second operating wavelength of said laser transmitter for excitation of fluorescence in said target volume;
measuring a second emission spectra of the excited target volume derived from said second operating wavelength;
comparing said first and second emission spectra to analyze said target volume.

12. The method of claim 11 wherein said target volume comprises an oil slick wherein:
said comparing step identifies at least one parameter of the oil in said oil slick.

13. The method of claim 1 including the step of:
calibrating the operating wavelength of said laser transmitter means using laser wavemeter means and comparing an output from said laser wavemeter means with an output from said spectrometer means.

14. The method of claim 1 wherein:
said selected spectra comprise Raman scattering spectra.

15. The method of claim 14 including the step of:
passing said detected pulses of light through laser line rejection filter means to improve said Raman scattering spectra.

16. The method of claim 15 including the step of:
positioning said laser line rejection filter either before said gated detector means or before said spectrometer means.

17. The method of claim 14 wherein said reflected pulses of light include Raman scattering spectra and spontaneous electronic emission spectra which has larger cross-sections than said Raman scattering spectra and including the step of:
rejecting said spontaneous electronic emission spectra from said Raman scattering spectra to improve said Raman scattering spectra.

18. The method of claim 17 wherein:
said rejecting step is accomplished by selected time delay of said gated detector means.

19. The method of claim 18 wherein said projecting step includes the step of projecting said pulses of light through a first variable field-of-view telescope and wherein said receiving step includes the step of:
receiving said reflected pulses of light in a second variable field-of-view telescope.

20. The method of claim 19 including:
adjusting the field-of-view in said first and second telescopes to increase laser power density of said laser transmitter means.

21. The method of claim 1 wherein said projecting step includes the step of projecting said pulses of light through variable field-of-view telescope means and wherein said receiving step includes the step of receiving said reflected pulses of light from said variable field-of-view telescope means.

22. The method of claim 14 including the step of:
non-linearly optically shifting said laser transmitter means to thereby shorten wavelengths of pulsed light generated by said laser transmitter means thereby improving said Raman scattering spectra.

23. The method of claim 19 including the step of:
narrowing the field-of-view of said second telescope to match the field-of-view of said first telescope.

24. The method of claim 1 wherein:
said spectrometer means comprises flat field monolithic spectrometer means.

25. The method of claim 1 including the steps of:
anamorphically demagnifying said reflected light pulses to slit shaped light pulses; and
delivering said slit shaped light pulses to an input slit in said spectrometer means.

26. The method of claim 1 wherein said spectrometer means comprises:
laser line rejection filter means;
diffraction grating means in optical communication with said rejection filter means; and
detector array means in optical communication with said diffraction grating means.

27. The method of claim 26 including:
at least one prism pre-disperser communication with said laser line rejection filter means.

28. The method of claim 1 wherein said spectrometer means comprises:
laser line rejection filter means;
at least one prism dispersion means in optical communication with said rejection filter means;
intensifier means in optical communication with said prism disperser means; and
detector array means in optical communication with said intensifer means.

29. A method for remotely and non-destructively probing the spectrally, temporally and distance-dependent optical properties of a target volume using a single integrated optical sensor having multiple modes of operation including an imaging mode and a spectral analysis mode, including the steps of:

selecting a mode of operation for the optical sensor to operate in an imaging mode or a temporal luminescence decay measurement mode, including the steps of:

selecting a mode of operation for the optical sensor to operate in an imaging mode or a temporal luminescence decay measurement mode with said imaging mode including steps (a)-(e) and said temporal luminescence decay measurement mode including steps (f)-(i):

(a) selectively generating short pulses of light using laser transmitter means;

(b) projecting said short pulses of light toward the backscattering medium and at a target volume enveloped by the medium;

(c) receiving said pulses of light backscattered from said target volume after a time delay corresponding to the round-trip propagation time of said light pulses to and from said target volume using receiver means;

(d) converting said received pulses of light to a video image of said target defining a target volume image, said target volume image having an image intensity pattern associated therewith; and (e) scanning the wavelength of the laser transmitter means to identify the wavelength-dependent differences in said image intensity pattern to thereby improve said video image of said target volume image;

(f) generating short pulses of light from laser transmitter means;

(g) projecting said generated short pulses of light toward a target volume;

(h) detecting said pulses of light backscattered from said target volume after a selected time delay using gated detector means; and (i) sweeping the selected time delay of said gated detector means for measuring the temporal luminescence decay of said target volume.

30. The method of claim 29 including the step of:
spatially resolving said temporal decay.

31. The method of claim 29 including the step of:
spectrally resolving said temporal decay.

32. The method of claim 29 wherein:
said luminescence temporal decay comprises fluorescence decay.

33. The method of claim 32 including the step of:
spectrally resolving said luminescence temporal decay at at least two different excitation wavelengths.

34. The method of claim 31 wherein said step of spectrally resolving said temporal decay utilizes an optical system comprising:
laser line rejection filter means;
at least one dispersive prism means in optical communication with said filter means;
streak camera tube means in optical communication with said dispersive prism means; and
detector array means in optical communication with said streak camera tube means.

35. The method of claim 34 including:
a plurality of dispersive prism means.

36. An apparatus for remotely and non-destructively probing the spectrally, temporally and distance-dependent optical properties of a target volume including:

a single, integrated optical sensor having multiple modes of operation including an imaging mode and a spectral analysis mode;

mode selection means for selecting a mode of operation for the optical sensor to operate in an imaging mode or a spectral analysis mode;

said imaging mode including;

(a) laser transmitting means for selectively generating short pulses of light;

(b) means for projecting said short pulses of light toward the backscattering medium and at a target volume enveloped by the medium;

(c) means for receiving said pulses of light backscattered from said target volume after a a time delay corresponding to the round-trip propagation time of said light pulses to and from said target volume using receiver means;

(d) means for converting said received pulses of light to a video image of said target defining a target volume image, said target volume image having an image intensity pattern associated therewith; and (e) means for scanning the wavelength of the laser transmitter means to identify the wavelength-dependent differences in said image intensity pattern to thereby improve said video image of said target volume image;

said spectral analysis mode including;

(f) laser transmitting means for generating short pulses of light;

(g) means for projecting said generated short pulses of light toward a target volume;

(h) means for detecting said pulses of light backscattered from said target volume after a selected time delay using gated detector means; and (i) spectrometer means for spectrally analyzing said detected pulses of light to create a selected spectra of said target volume.

37. The apparatus of claim 36 wherein in said imaging mode:
said laser transmitter means has an operating wavelength and includes means for tuning said operating wavelength.

38. The apparatus of claim 36 wherein in said imaging mode said means for projecting includes a first variable field-of-view telescope and wherein said means for receiving includes a second variable field-of-view telescope.

39. The apparatus of claim 36 wherein in said imaging mode said means for projecting includes variable field-of-view telescope means and wherein said means for receiving includes said variable field-of-view telescope means.

40. The apparatus of claim 36 wherein in said imaging mode said means for scanning is controlled by at least one of the wavelength controlling means selected from the group consisting of harmonic generator means, Raman shifter means and optical parameter oscillator means.

41. The apparatus of claim 36 wherein said selected spectra comprises emission spectra and including:
means for selecting the operating wavelength of said laser transmitter means for excitation of fluorescence in said target volume and;
means for measuring the emission spectra to analyze said target volume.

42. The apparatus of claim 41 wherein:
means for analyzing said emission spectra for detection of chemical species in said target volume.

43. The apparatus of claim 36 wherein said selected spectra comprises excitation spectra and including:
   means for selecting a first operating wavelength of said laser transmitter for excitation of fluorescence in said target volume;
   means for measuring a first emission spectra of the excited target volume derived from said first operating wavelength;
   means for selecting a second operating wavelength of said laser transmitter for excitation of fluorescence in said target volume;
   means for measuring a second emission spectra of the excited target volume derived from said second operating wavelength;
   means for comparing said first and second emission spectra to analyze said target volume.

44. The apparatus of claim 36 including:
   means for calibrating the operating wavelength of said laser transmitter means using laser wavemeter means and comparing an output from said laser wavemeter means with an output from said spectrometer means.

45. The apparatus of claim 36 wherein said selected spectra comprise Raman scattering spectra and including:
   laser line rejection filter means for receiving said detected pulses of light and thereby improving said Raman scattering spectra.

46. The apparatus of claim 45 wherein:
   said laser line rejection filter is positioned either before said gated detector means or before said spectrometer means.

47. The apparatus of claim 36 wherein said means for projecting includes a first variable field-of-view telescope and wherein said means for receiving includes a second variable field-of-view telescope.

48. The apparatus of claim 36 wherein said means for projecting includes variable field-of-view telescope means and wherein said means for receiving includes said variable field-of-view telescope means.

49. The apparatus of claim 36 wherein:
   said spectrometer means comprises flat field monolithic spectrometer means.

50. The apparatus of claim 36 including:
   means for anamorphically demagnifying said reflected light pulses to slit shaped light pulses; and
   means for delivering said slit shaped light pulses to an input slit in said spectrometer means.

51. The apparatus of claim 36 wherein said spectrometer means comprises:
   laser line rejection filter means;
   diffraction grating means in optical communication with said rejection filter means; and
   detector array means in optical communication with said diffraction grating means.

52. The apparatus of claim 51 including:
   at least one prism pre-disperser means in input optical communication with said laser line rejection filter means.

53. The apparatus of claim 36 wherein said spectrometer means comprises:
   laser line rejection filter means;
   at least one prism dispersion means in optical communication with said rejection filter means;
   intensifier means in optical communication with said prism disperser means; and
   detector array means in optical communication with said intensifer means.

54. An apparatus for remotely and non-destructively probing the spectrally, temporally and distance-dependent optical properties of a target volume including:
   a single, integrated optical sensor having multiple modes of operation including an imaging mode and a temporal luminescence decay measurement mode;
   mode selection means for selecting a mode of operation for the optical sensor to operate in an imaging mode or a temporal luminescence decay measurement mode;
   said imaging mode including;
   (a) laser transmitting means for selectively generating short pulses of light;
   (b) means for projecting said short pulses of light toward the backscattering medium and at a target volume enveloped by the medium;
   (c) means for receiving said pulses of light backscattered from said target volume after a a time delay corresponding to the round-trip propagation time of said light pulses to and from said target volume using receiver means;
   (d) means for converting said received pulses of light to a video image of said target defining a target volume image, said target volume image having an image intensity pattern associated therewith; and
   (e) means for scanning the wavelength of the laser transmitter means to identify the wavelength-dependent differences in said image intensity pattern to thereby improve said video image of said target volume image;
   said temporal luminescence decay measurement mode including;
   (f) laser transmitter means for generating short pulses of light;
   (g) means for projecting said generated short pulses of light toward the said target volume;
   (h) means for detecting said pulses of light backscattered from said target volume after using a selected time delay using gated detector means; and
   (i) means for sweeping the selected time delay of said gated detector means for measuring the temporal luminescence decay of said target volume.

55. The apparatus of claim 54 including:
   means for spatially resolving said temporal decay.

56. The apparatus of claim 54 including:
   means for spectrally resolving said temporal decay.

57. The apparatus of claim 56 wherein said luminescence temporal decay comprises fluorescence decay and including:
   means for spectrally resolving said luminescence temporal decay at at least two different excitation wavelengths.

58. The apparatus of claim 56 wherein said means for spectrally resolving said temporal decay utilizes an optical system comprising:
   laser line rejection filter means;
   at least one dispersive prism means in optical communication with said filter means;
   streak camera tube means in optical communication with said dispersive prism means; and
   detector array means in optical communication with said streak camera tube means.

59. The apparatus of claim 58 including:
   a plurality of dispersive prism means.

* * * * *